(12) United States Patent  (10) Patent No.: US 8,338,480 B2
von Borstel et al.  (45) Date of Patent: *Dec. 25, 2012

(54) COMBINATION TREATMENT OF METABOLIC DISORDERS

(75) Inventors: Reid W. von Borstel, Potomac, MD (US); Kirvin L. Hodge, Laurel, MD (US)

(73) Assignee: Wellstat Therapeutics Corporation, Gaithersburg, MD (US)

( * ) Notice: Subject to any disclaimer, the term of this patent is extended or adjusted under 35 U.S.C. 154(b) by 459 days.

This patent is subject to a terminal disclaimer.

(21) Appl. No.: 12/294,530

(22) PCT Filed: Mar. 5, 2007

(86) PCT No.: PCT/US2007/063288
§ 371 (c)(1),
(2), (4) Date: Jul. 23, 2010

(87) PCT Pub. No.: WO2007/117791
PCT Pub. Date: Oct. 18, 2007

(65) Prior Publication Data
US 2010/0292277 A1 Nov. 18, 2010

Related U.S. Application Data

(60) Provisional application No. 60/744,021, filed on Mar. 31, 2006.

(51) Int. Cl.
*A61K 31/24* (2006.01)
*A61K 31/505* (2006.01)
*A61K 31/44* (2006.01)
*A61K 31/425* (2006.01)
*A61K 31/20* (2006.01)

(52) U.S. Cl. ........ 514/541; 514/275; 514/342; 514/367; 514/560; 514/866

(58) Field of Classification Search .................. 514/541, 514/560, 275, 342, 367, 866
See application file for complete search history.

(56) References Cited

U.S. PATENT DOCUMENTS

| | | | |
|---|---|---|---|
| 5,002,953 | A | 3/1991 | Hindley |
| 5,965,584 | A | 10/1999 | Ikeda et al. |
| 6,166,042 | A | 12/2000 | Ikeda et al. |
| 6,172,046 | B1 | 1/2001 | Albrecht |
| 6,472,373 | B1 | 10/2002 | Albrecht |
| 6,858,602 | B2 | 2/2005 | Sharma et al. |
| 6,916,848 | B2 | 7/2005 | Sharma |
| 6,924,314 | B2 | 8/2005 | Sharma et al. |
| 6,946,491 | B2 | 9/2005 | Sharma et al. |
| 7,012,071 | B2 | 3/2006 | Sharma et al. |
| 7,041,659 | B2 | 5/2006 | Sharma |
| 7,045,541 | B2 | 5/2006 | Sharma |
| 7,101,910 | B2 | 9/2006 | Sharma |
| 7,329,782 | B2 | 2/2008 | Sharma et al. |
| 7,361,686 | B2 | 4/2008 | Hodge et al. |
| 7,442,796 | B2 | 10/2008 | Sharma et al. |
| 7,605,181 | B2 | 10/2009 | Hodge et al. |
| 7,932,290 | B2 * | 4/2011 | Hodge et al. .................. 514/570 |
| 8,022,249 | B2 * | 9/2011 | Sharma et al. ............... 562/621 |
| 2005/0020684 | A1 | 1/2005 | Brooks et al. |
| 2005/0090555 | A1 | 4/2005 | Sharma et al. |
| 2006/0014784 | A1 | 1/2006 | Hodge et al. |
| 2006/0035970 | A1 | 2/2006 | Hodge et al. |
| 2006/0247309 | A1 | 11/2006 | Hodge et al. |
| 2007/0105958 | A1 | 5/2007 | Sharma et al. |
| 2007/0249696 | A1 | 10/2007 | Sharma et al. |
| 2007/0249719 | A1 | 10/2007 | Sharma et al. |

(Continued)

FOREIGN PATENT DOCUMENTS

WO 02/100341 A2 12/2002

(Continued)

OTHER PUBLICATIONS

Bandgar, et al., "Direct synthesis of 2-oxazolines from carboxylic acids using 2-chloro-4,6-dimethoxy-1,3,5-triazine under mild conditions", Tetrahedron Letters, 44:2331-2333, 2003.
Rosiglitazone (Systemic), Drug Information Sheet, Medline Plus, pp. 1-5, 2004.
RN:12320-73-4 Rosiglitazone, ChemIDplus Advanced, National Library of Medicine, Specialized Information Services, p. 1, 2004.
Avandia (rosiglitazone maleate), Drug Information Sheet, RxList The Internet Drug Index, pp. 1-6, 2005.
RN:111025-46-8 Pioglitazone [BAN:INN], ChemIDplus Advanced, National Library of Medicine, Specialized Information Services, p. 1, 2004.

(Continued)

*Primary Examiner* — Kevin E Weddington
(74) *Attorney, Agent, or Firm* — Lewis J. Kreisler

(57) ABSTRACT

Various metabolic disorders, such as insulin resistance syndrome, diabetes, polycystic ovary syndrome, hyperlipidemia, fatty liver disease, cachexia, obesity, atherosclerosis and arteriosclerosis can be treated with a combination of a direct PPAR-gamma agonist and a Compound of Formula (I) or a pharmaceutically acceptable salt thereof (I) Three of $R^1$, $R^2$, $R^3$, $R^4$ and $R^5$ are hydrogen and the remainder are independently selected from the group consisting of hydrogen, halo, hydroxy, methyl, ethyl, perfluoromethyl, methoxy, ethoxy, and perfluoromethoxy; and m is 0, 2 or 4. $R^6$ is hydrogen, O or hydroxy, and X is $—OR^7$, wherein $R^7$ is hydrogen or alkyl having from 1 to 3 carbon atoms; or $R^6$ is hydrogen, and X is $—NR^8R^9$, wherein $R^8$ is hydrogen or hydroxy and $R^9$ is hydrogen, methyl or ethyl. When X is $—NR^8R^9$, hydroxy none of $R^1$, $R^2$, $R^3$, $R^4$ and $R^5$ is hydroxy.

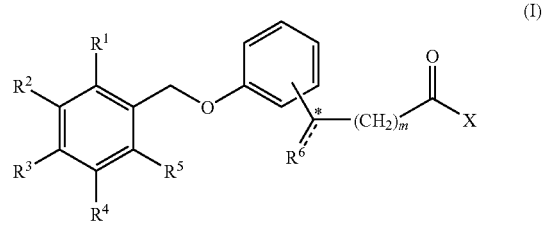

(I)

14 Claims, No Drawings

U.S. PATENT DOCUMENTS

| | | |
|---|---|---|
| 2007/0265322 A1 | 11/2007 | Sharma et al. |
| 2007/0282003 A1 | 12/2007 | Sharma et al. |
| 2008/0015209 A1 | 1/2008 | Sharma et al. |
| 2008/0015254 A1 | 1/2008 | Sharma et al. |
| 2008/0021109 A1 | 1/2008 | Sharma et al. |
| 2008/0027229 A1 | 1/2008 | Hodge et al. |
| 2008/0306150 A1 | 12/2008 | Sharma et al. |
| 2008/0306165 A1 | 12/2008 | Sharma et al. |

FOREIGN PATENT DOCUMENTS

| | | |
|---|---|---|
| WO | 2004/073611 A2 | 9/2004 |
| WO | 2004/091486 A2 | 10/2004 |
| WO | 2006/127133 A2 | 11/2006 |
| WO | 2007/087506 A2 | 8/2007 |

OTHER PUBLICATIONS

Pioglitazone Drug Information Sheet, Medline Plus, pp. 1-4, 2005.
ACTOS (pioglitazone hydrochloride), Drug Information Sheet, RxList The Internet Drug Index, pp. 1-2, 2004.
Troglitazone (Systemic), Drug Information Sheet, Medline Plus, pp. 1-4, 2000.
Pending (as of Mar. 24, 2008) claims from U.S. Appl. No. 11/772,515.
Pending (as of Mar. 24, 2008) claims from U.S. Appl. No. 11/772,520.
Pending (as of Mar. 24, 2008) claims from U.S. Appl. No. 11/772,560.
Pending (as of Jul. 14, 2008) claims from U.S. Appl. No. 12/160,857.
Pending (as of Jul. 28, 2008) claims from U.S. Appl. No. 12/162,397.
Pending (as of May 7, 2008) claims from U.S. Appl. No. 12/092,932.
Pending (as of Aug. 13, 2008) claims from U.S. Appl. No. 12/279,247.
Pending (as of Aug. 18, 2008) claims from U.S. Appl. No. 12/160,808.
Pending (as of Nov. 10, 2008) claims from U.S. Appl. No. 12/300,239.
Younis, et al., "The prevention of type 2 diabetes mellitus: recent advances", QJ Med., vol. 97, pp. 451-455, 2004.
Goff, et al., "Prevention of Cardiovascular Disease in Persons with type 2 diabetes Mellitus: Current Knowledge and Rational for the Action to Control Cardiovascular Risk in Diabetes (ACCORD) Trial", Am J Cardiol., 99(12A): S4-S20, 2007. (Abstract).
Knowler, et al., "Perspectives in Diabetes: Preventing Non-Insulin-Dependent Diabetes", Diabetes, vol. 44, pp. 483-488, 1995.
Chu, et al., "Effective Rosiglitazone Alone and in Combination with Atorvastatin on Nontraditional Markers of Cardiovascular Disease in Patients with Type 2 Diabetes Mellitus", American Journal of Cardiology, 97(5): 646-650, 2006.
Del Prato, et al., "Rosiglitazone plus metformin: combination therapy for Type 2 Diabetes", Expert Opinion on Pharmacotherapy, 5(6):1411-1422, 2004.
Proost, et al., "MW/Pharm, an Integrated Software Package for Drug Dosage Regimen Calculation and Therapeutic Drug Monitoring", Computers in Biology and Medicine, 22(3): 155-163, 1992.

* cited by examiner

COMBINATION TREATMENT OF METABOLIC DISORDERS

BACKGROUND OF THE INVENTION

Diabetes remains a major and growing public health problem. Late stage complications of diabetes consume a large proportion of national health care resources.

Drugs acting as agonists toward PPAR-gamma (Peroxisome Proliferation Activator Receptor-gamma) are useful for treatment of Type 2 diabetes. They lower blood glucose and clear lipids contributing to insulin resistance from muscle, though at the expense of increased subcutaneous fat deposition and weight gain. Clinical use of PPAR-gamma agonists is also limited by fluid retention, increasing the risk of heart failure. In animals, doses of PPAR-gamma agonists within or only slightly outside the therapeutic range cause cardiac enlargement. There is a need for new therapies that effectively address the primary defects of insulin resistance and islet failure with fewer or milder side effects than existing drugs.

The use of certain compounds in combination with rosiglitazone or pioglitazone is disclosed in WO 02/100341, WO/073611, WO 04/091486, U.S. Provisional Patent Applications No. 60/667,457, filed Apr. 1, 2005, and No. 60/762,068, filed Jan. 25, 2006, all of which are assigned to Wellstat Therapeutics Corp.

Rosiglitazone, a direct PPAR-gamma agonist, is marketed in combination with other antidiabetes drugs as AVANDAMET® (rosiglitazone maleate and metformin hydrochloride) and as AVANDARYL® (rosiglitazone maleate and glimepride).

SUMMARY OF THE INVENTION

This invention concerns therapeutic uses of a combination of a direct PPAR-gamma agonist and a Compound of Formula I or a pharmaceutically acceptable salt thereof.

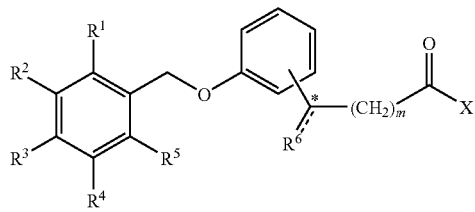

(I)

In Formula I, m is 0, 2 or 4. X is —$OR^7$, wherein $R^7$ is hydrogen or alkyl having from 1 to 3 carbon atoms; $R^6$ is hydrogen, O or hydroxy; and three of $R^1$, $R^2$, $R^3$, $R^4$ and $R^5$ are hydrogen and the remainder are independently selected from the group consisting of hydrogen, halo, hydroxy, methyl, ethyl, perfluoromethyl, methoxy, ethoxy, and perfluoromethoxy. Alternatively X is —$NR^8R^9$, wherein $R^8$ is hydrogen or hydroxy and $R^9$ is hydrogen, methyl or ethyl; $R^6$ is hydrogen; and three of $R^1$, $R^2$, $R^3$, $R^4$ and $R^5$ are hydrogen and the remainder are independently selected from the group consisting of hydrogen, halo, methyl, ethyl, perfluoromethyl, methoxy, ethoxy, and perfluoromethoxy.

This invention provides a method of treating a mammalian subject having a condition selected from the group consisting of insulin resistance syndrome, diabetes, polycystic ovary syndrome, hyperlipidemia, fatty liver disease, cachexia, obesity, atherosclerosis and arteriosclerosis, comprising administering to the subject a Compound of Formula I or a pharmaceutically acceptable salt thereof and a direct PPAR-gamma agonist in a combined amount effective to treat the metabolic condition.

This invention provides the use of a biologically active agent in the manufacture of a medicament for treatment of a condition selected from the group consisting of insulin resistance syndrome, diabetes including Type I Diabetes and Type II Diabetes, and polycystic ovary syndrome; or for the treatment or reduction in the chance of developing atherosclerosis, arteriosclerosis, obesity, hypertension, hyperlipidemia, fatty liver disease, nephropathy, neuropathy, retinopathy, foot ulceration or cataracts associated with diabetes; or for the treatment of a condition selected from the group consisting of hyperlipidemia, cachexia, and obesity; wherein the agent is a Compound of Formula I or a pharmaceutically acceptable salt thereof and is formulated for use in combination with a direct PPAR-gamma agonist in a combined amount effective to treat the metabolic condition.

This invention provides a pharmaceutical composition for use in the treatment of a condition selected from the group consisting of insulin resistance syndrome, diabetes, polycystic ovary syndrome, hyperlipidemia, fatty liver disease, cachexia, obesity, atherosclerosis, arteriosclerosis, comprising a Compound of Formula I or a pharmaceutically acceptable salt thereof and a direct PPAR-gamma agonist in a combined amount effective to treat the condition.

A kit comprising one or more unit oral doses of a Compound of Formula I or a pharmaceutically acceptable salt thereof, one or more unit oral doses of a direct PPAR-gamma agonist, and instructions for administering the Compound of Formula I or pharmaceutically acceptable salt thereof in combination with the direct PPAR-gamma agonist.

This invention is based in part on the observation that when obese, diabetic mice are treated with a combination of a low dose (e.g. 3 mg/kg/day) of a direct PPAR-gamma agonist, such as rosiglitazone (RSG), and a low dose of a compound of formula I, such as Compound BI (e.g. 30 mg/kg/day), blood glucose can be reduced to levels lower than can be achieved with high doses of either agent.

Furthermore, combined treatment utilizing a low dose (30 mg/kg) of a compound of Formula I, such as Compound BI (which by itself had little effect on body weight and food intake), and a low dose of a direct PPAR-gamma agonist, such as RSG (3 mg/kg) (which by itself did not attenuate body weight gain or food intake), resulted in a substantial loss of body weight and food consumption. Raising the dose of either drug in the combination induced an increase in food intake relative to the effect of low doses of both drugs. This indicates that the reduced appetite was not due to toxic anorexia, but is more likely through modification of appetite regulatory mechanisms.

By improving the antidiabetic efficacy of low doses of direct PPAR-gamma agonists, their side effects (e.g. weight gain and edema) are minimized while still retaining their therapeutic benefits. This opens up the opportunity for wider application of direct PPAR-gamma agonists in pre-diabetic conditions ("metabolic syndrome" or "impaired glucose tolerance") where safety concerns about side effects have heretofore limited their use. Furthermore, the observation that the combination of a Compound of Formula I, such as Compound BI, and a direct PPAR-gamma agonist, such as RSG, resulted in major attenuation of appetite and a reduction in body weight in genetically obese mice demonstrates the usefulness of such combination treatment against obesity and its health consequences.

DETAILED DESCRIPTION OF THE INVENTION

Definitions

As used herein the term "alkyl" means a linear or branched-chain alkyl group. An alkyl group identified as having a certain number of carbon atoms means any alkyl group having the specified number of carbons. For example, an alkyl having three carbon atoms can be propyl or isopropyl; and alkyl having four carbon atoms can be n-butyl, 1-methylpropyl, 2-methylpropyl or t-butyl.

As used herein the term "halo" refers to one or more of fluoro, chloro, bromo, and iodo.

As used herein the term "perfluoro" as in perfluoromethyl or perfluoromethoxy, means that the group in question has fluorine atoms in place of all of the hydrogen atoms.

As used herein "Ac" refers to the group $CH_3C(O)$—.

The bond between $R^6$ and the carbon atom to which it is directly bonded is depicted in Formula I above by a solid line together with a dashed line. This depiction reflects that the bond in question can be either a single bond, when $R^6$ is hydrogen or hydroxy, or a double bond, when $R^6$ is O.

The asterisk in the depiction of Formula I above indicates a possible chiral center, and that carbon is chiral when $R^6$ is hydroxy. In such cases, this invention provides the racemate, the (R) enantiomer, and the (S) enantiomer, of the Compounds of Formula I, all of which are believed to be active. Mixtures of these enantiomers can be separated by using HPLC, for example as described in Chirality 11:420-425 (1999).

Certain chemical Compounds are referred to herein by their chemical name or by the two-letter code shown below. Compounds BI, CF, CR and CT are included within the scope of Formula I shown above.

BI 4-(3-(2,6-Dimethylbenzyloxy)phenyl)-4-oxobutyric acid
CF 3-(2,6-Dimethylbenzyloxy)phenylacetic acid
CR 4-(3-(2,6-Dimethylbenzyloxy)-phenyl)-4(R)-hydroxybutanoic acid
CT N-Hydroxy-2-[3-(2,6-dimethylbenzyloxy)phenyl]acetamide As used herein the term "direct PPAR-gamma agonist" means an agent whose primary mechanism of action involves binding to and increasing the activity of the Peroxisome Proliferation Activator Receptor-gamma (PPAR-γ). PPAR-gamma activation can be measured in a variety of ways, including by direct assay, by transactivation assy, or by measuring a change in activity of genes or gene products that are regulated by PPAR-gamma.

As used herein the abbreviation "RSG" refers to rosiglitazone. In the Examples, references to RSG or rosiglitazone refer to rosiglitazone maleate, also known by its tradename AVANDIA®. As used herein the abbreviation "PIO" refers to pioglitazone. In the Examples, references to PIO or pioglitazone hydrochloride, also known by its tradename ACTOS®. As used herein the abbreviation "PYY" refers to Peptide YY fragment 3-36 human. PYY and Cerulenin are available from Sigma.

As used herein the transitional term "comprising" is open-ended. A claim utilizing this term can contain elements in addition to those recited in such claim.

Compounds of the Invention

In an embodiment of the invention described in the Summary above, $R^1$ is methyl and $R^5$ is methyl. In another embodiment X is —$OR^7$, wherein $R^7$ is hydrogen or alkyl having from 1 to 3 carbon atoms. In another embodiment X is —$NR^8R^9$, wherein $R^8$ is hydrogen or hydroxy and $R^9$ is hydrogen, methyl or ethyl.

In a further embodiment of the invention described in the Summary above, the direct PPAR-gamma agonist is combined with a compound of formula IA or a pharmaceutically acceptable salt thereof.

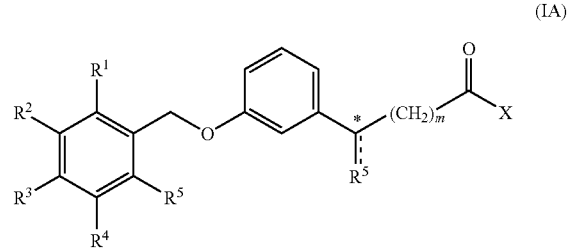

(IA)

In Formula IA the variables have the same values as described above in connection with Formula I. Preferably $R^1$ is methyl and $R^5$ is methyl. Examples of such Compounds include compounds BI, CF, CR and CT.

The compounds of Formula I can be made according to methods described in WO 02/100341, WO/073611, WO 04/091486, U.S. Provisional Patent Applications No. 60/667,457, filed Apr. 1, 2005, and No. 60/762,068, filed Jan. 25, 2006, the contents of which are incorporated herein by reference.

In accordance with the invention described above any direct PPAR-gamma agonist can be utilized. Examples of such direct PPAR-gamma agonists include rosiglitazone and pioglitazone, their pharmaceutically acceptable salts, as well as hydrates and solvates of such compounds and such salts. The maleate salt of rosiglitazone is currently marketed under the tradename AVANDIA® (GlaxoSmithKline). Pioglitazone hydrochloride is currently marketed under the tradename ACTOS® (Eli Lilly and Co.). Other examples of direct PPAR-gamma agonists include 5-[(2,4-dioxothiazolidin-5-yl)methyl]-2-methoxy-N-[[4-(trifluoromethyl)-phenyl]methyl]benzamide (KRP-297; Kyorin/Merck; Murakami, et al., Metabolism. 1999 November; 48(11):1450-4); ((+)-[[6-(2-fluorbenzyl)-oxy-2-naphy]methyl]-2,4-thiazolidinedione) (MCC-555; Mitsubishi/J&J; Upton, et al., Br J Pharmacol. 1998 December; 125(8): 1708-14); (4-[4-[2-(5-methyl-2-phenyl-4-oxazolyl)ethoxy]benzyl]-3,5-isoxazolidinedione)) (PNU-1827/JTT-501; Pharmacia/Japan Tobacco; Shibata, et al., Eur J Pharmacol. 1999 Jan. 8; 364(2-3):211-9); (−)3-[4-[2-(Phenoxazin-10-yl)ethoxy]phenyl]-2-ethoxypropanoic acid (DRF-2725; Novo Nordisk/Doctor Reddy Foundation; Lohray, et al., J Med Chem. 2001 Aug. 2; 44(16):2675-8); ([5-[4-[2-(1-indolyl)ethoxy]phenyl]methyl]thiazolidine-2,4-dione (DRF-2189; Doctor Reddy Foundation; Chakrabarti, et al., Arzneimittelforschung. 1999 November; 49(11):905-11); ((Z)-1,4-bis[4-[(3,5-dioxo-1,2,4-oxadiazolidin-2-yl)methyl]phenoxy]but-2-ene) (YM-440; Yamanouchi; Shimaya, et al, Metabolism. 2000 March; 49(3):411-7); (5-[4-[2-(5 methyl-2-phenyl-4-oxazolyl)-2-hydroxyethoxy]benzyl]-2,4-thiazolidinedione) (AD-5075; Daiichi; Zhang, et al., J Biol. Chem. 1996 Apr. 19; 271(16):9455-9); (S)-2-ethoxy-3-[4-[2-(4-methylsulphonyloxyphenyl)ethoxy]phenyl]propanoic acid (AZ-242; AstraZeneca); and {[±]-5-[(7-benzyloxy-3-quinolyl)methyl]-2,4-thiazolidinedione} (NC2100; Fukui, et al., Diabetes. 2000 May; 49(5):759-67).

Use in Methods of Treatment

This invention provides a method for treating a mammalian subject with a condition selected from the group consisting of insulin resistance syndrome, diabetes (both primary essential diabetes such as Type I Diabetes or Type II Diabetes and secondary nonessential diabetes) and polycystic ovary syndrome, comprising administering to the subject a compound of Formula I or pharmaceutically acceptable salt thereof and a direct PPAR-gamma agonist in a combined amount effective to treat the condition. In accordance with the method of this invention a symptom of diabetes or the chance of developing a symptom of diabetes, such as atherosclerosis, obesity, hypertension, hyperlipidemia, fatty liver disease, nephropathy, neuropathy, retinopathy, foot ulceration and cataracts, each such symptom being associated with diabetes, can be reduced. This invention also provides a method for treating hyperlipidemia comprising administering to the subject an amount of a biologically active agent as described herein effective to treat the condition. Compounds reduce serum triglycerides and free fatty acids in hyperlipidemic animals. This invention also provides a method for treating cachexia comprising administering to the subject an amount of a biologically active agent as described herein effective to treat the cachexia. This invention also provides a method for treating obesity comprising administering to the subject an amount of a biologically active agent as described herein effective to treat the condition. This invention also provides a method for treating a condition selected from atherosclerosis or arteriosclerosis comprising administering to the subject an amount of a biologically active agent as described herein effective to treat the condition. The active agents of this invention are effective to treat hyperlipidemia, fatty liver disease, cachexia, obesity, atherosclerosis or arteriosclerosis whether or not the subject has diabetes or insulin resistance syndrome. The Compound of Formula I or salt thereof and the direct PPAR-gamma agonist can be administered by any conventional route of systemic administration. Preferably they are administered orally. Accordingly, it is preferred for the medicament to be formulated for oral administration. Other routes of administration that can be used in accordance with this invention include rectally, parenterally, by injection (e.g. intravenous, subcutaneous, intramuscular or intraperitioneal injection), or nasally.

Further embodiments of each of the uses and methods of treatment of this invention comprise administering any of the embodiments of the Compound of Formula I or pharmaceutically salts thereof and any of the direct PPAR-gamma agonists described above. In the interest of avoiding unnecessary redundancy, each such agent and group of agents is not being repeated, but they are incorporated into this description of uses and methods of treatment as if they were repeated.

Many of the diseases or disorders that are addressed by this invention fall into two broad categories: Insulin resistance syndromes and consequences of chronic hyperglycemia. Dysregulation of fuel metabolism, especially insulin resistance, which can occur in the absence of diabetes (persistent hyperglycemia) per se, is associated with a variety of symptoms, including hyperlipidemia, atherosclerosis, obesity, essential hypertension, fatty liver disease (NASH; nonalcoholic steatohepatitis), and, especially in the context of cancer or systemic inflammatory disease, cachexia. Cachexia can also occur in the context of Type I Diabetes or late-stage Type II Diabetes. By improving tissue fuel metabolism, active agents of the invention are useful for preventing or ameliorating diseases and symptoms associated with insulin resistance. While a cluster of signs and symptoms associated with insulin resistance may coexist in an individual patient, it many cases only one symptom may dominate, due to individual differences in vulnerability of the many physiological systems affected by insulin resistance. Nonetheless, since insulin resistance is a major contributor to many disease conditions, drugs which address this cellular and molecular defect are useful for prevention or amelioration of virtually any symptom in any organ system that may be due to, or exacerbated by, insulin resistance.

When insulin resistance and concurrent inadequate insulin production by pancreatic islets are sufficiently severe, chronic hyperglycemia occurs, defining the onset of Type II diabetes mellitus (NIDDM). In addition to the metabolic disorders related to insulin resistance indicated above, disease symptoms secondary to hyperglycemia also occur in patients with NIDDM. These include nephropathy, peripheral neuropathy, retinopathy, microvascular disease, ulceration of the extremities, and consequences of nonenzymatic glycosylation of proteins, e.g. damage to collagen and other connective tissues. Attenuation of hyperglycemia reduces the rate of onset and severity of these consequences of diabetes. Because active agents and compositions of the invention help to reduce hyperglycemia in diabetes, they are useful for prevention and amelioration of complications of chronic hyperglycemia.

Both human and non-human mammalian subjects can be treated in accordance with the treatment method of this invention. The optimal dose of a particular active agent of the invention for a particular subject can be determined in the clinical setting by a skilled clinician. In the case of oral administration to a human for treatment of disorders related to insulin resistance, diabetes, hyperlipidemia, fatty liver disease, cachexia or obesity the Compound of Formula I or pharmaceutically acceptable salt thereof is generally administered in a daily dose of from 1 mg to 400 mg, more preferably from 200 mg to 400 mg, administered once or twice per day. In the case of oral administration to a mouse Compound of Formula I or pharmaceutically acceptable salt thereof is generally administered in a daily dose from 1 to 300 mg of the agent per kilogram of body weight. Direct PPAR-gamma agonists are administered in accord with standard clinical practice. In some cases, coadministration with a compound of Formula I or a pharmaceutically acceptable salt thereof will improve the efficacy of other classes of drugs, permitting lower (and therefore less toxic) doses of such agents to be administered to patients with satisfactory therapeutic results. Established safe and effective dose ranges in humans for representative compounds are: rosiglitazone (including rosiglitazone maleate) 4 to 8 mg/day; pioglitazone (including pioglitazone hydrochloride) 15 to 45 mg/day.

In an embodiment of this invention the dose of either or both of the Compound of Formula I and the PPAR-gamma agonist is less than the therapeutic dose when the drugs are used alone. Typically the dose can be reduced to between 25% and 75% of the usual dose. Thus, for example the daily dose of the Compound of Formula I can be from 50 mg to 150 mg. The daily dose of rosiglitazone can be from 1 mg to 3 mg, and the daily dose of pioglitazone can be from 3.75 mg to 11.25 mg. In an embodiment of this invention the dose of either or both of the Compound of Formula I and the PPAR-gamma agonist are chosen so that weight loss and/or appetite reduction result.

An admixture of the direct PPAR-gamma agonist and the compound or salt of Formula I can be administered to the subject. Alternatively the direct PPAR-gamma agonist and the compound or salt of Formula I are not mixed together to form an admixture but are administered independently to the subject. When the active ingredients are not mixed together to form a single admixture or composition it is convenient to provide them in the form of a kit comprising one or more unit oral doses of a Compound of Formula I or a pharmaceutically acceptable salt thereof, one or more unit oral doses of a direct PPAR-gamma agonist, and instructions for administering the Compound of Formula I or pharmaceutically acceptable salt thereof in combination with the direct PPAR-gamma agonist. Preferably the components of the kit are packaged together, such as in a box or a blister pack.

Type I Diabetes Mellitus: A patient with Type I diabetes manages their disease primarily by self-administration of one to several doses of insulin per day, with frequent monitoring blood glucose to permit appropriate adjustment of the dose and timing of insulin administration. Chronic hyperglycemia leads to complications such as nephropathy, neuropathy, retinopathy, foot ulceration, and early mortality; hypoglycemia due to excessive insulin dosing can cause cognitive dysfunction or unconsciousness. A patient with Type I diabetes is treated with a direct PPAR-gamma agonist and from 1 to 400 mg/day of the compound of Formula I or salt thereof, in tablet or capsule form, each drug separately as a single or a divided daily dose, or both drugs combined as a single or a divided daily dose. The anticipated effect will be a reduction in the dose or frequency of administration of insulin required to maintain blood glucose in a satisfactory range, and a reduced incidence and severity of hypoglycemic episodes. Clinical outcome is monitored by measurement of blood glucose and glycosylated hemoglobin (an index of adequacy of glycemic control integrated over a period of several months), as well as by reduced incidence and severity of typical complications of diabetes. The treatment of this invention can be administered in conjunction with islet transplantation to help maintain the anti-diabetic efficacy of the islet transplant.

Type II Diabetes Mellitus: A typical patient with Type II diabetes (NIDDM) manages their disease by programs of diet and exercise as well as by taking medications such as metformin, glyburide, repaglinide, rosiglitazone, or acarbose, all of which provide some improvement in glycemic control in some patients, but none of which are free of side effects or eventual treatment failure due to disease progression. Islet failure occurs over time in patients with NIDDM, necessitating insulin injections in a large fraction of patients. It is anticipated that daily treatment in accordance with this invention (with or without additional classes of antidiabetic medication) will improve glycemic control, reduce the rate of islet failure, and reduce the incidence and severity of typical symptoms of diabetes. In addition, elevated serum triglycerides and fatty acids will be reduced, thereby reducing the risk of cardiovascular disease, a major cause of death of diabetic patients. As is the case for all other therapeutic agents for diabetes, dose optimization is done in individual patients according to need, clinical effect, and susceptibility to side effects.

Hyperlipidemia: Elevated triglyceride and free fatty acid levels in blood affect a substantial fraction of the population and are an important risk factor for atherosclerosis and myocardial infarction. Treatment in accordance with this invention is useful for reducing circulating triglycerides and free fatty acids in hyperlipidemic patients. Hyperlipidemic patients often also have elevated blood cholesterol levels, which also increase the risk of cardiovascular disease. Cholesterol-lowering drugs such as HMG-CoA reductase inhibitors ("statins") can be administered to hyperlipidemic patients in addition to agents of the invention, optionally incorporated into the same pharmaceutical composition.

Fatty Liver Disease: A substantial fraction of the population is affected by fatty liver disease, also known as nonalcoholic steatohepatitis (NASH); NASH is often associated with obesity and diabetes. Hepatic steatosis, the presence of droplets of triglycerides with hepatocytes, predisposes the liver to chronic inflammation (detected in biopsy samples as infiltration of inflammatory leukocytes), which can lead to fibrosis and cirrhosis. Fatty liver disease is generally detected by observation of elevated serum levels of liver-specific enzymes such as the transaminases ALT and AST, which serve as indices of hepatocyte injury, as well as by presentation of symptoms which include fatigue and pain in the region of the liver, though definitive diagnosis often requires a biopsy. The anticipated benefit is a reduction in liver inflammation and fat content, resulting in attenuation, halting, or reversal of the progression of NASH toward fibrosis and cirrhosis.

Pharmaceutical Compositions

This invention provides a pharmaceutical composition comprising a compound of Formula I or a pharmaceutically acceptable salt thereof and a direct PPAR-gamma agonist, and optionally pharmaceutically acceptable carrier. Further embodiments of the pharmaceutical composition of this invention comprise any one of the embodiments of the biologically active agents described above. In the interest of avoiding unnecessary redundancy, each such agent and group of agents is not being repeated, but they are incorporated into this description of pharmaceutical compositions as if they were repeated.

Preferably the composition is adapted for oral administration, e.g. in the form of a tablet, coated tablet, dragee, hard or soft gelatin capsule, solution, emulsion or suspension. In general the oral composition will comprise, together with a direct PPAR-gamma agonist, from 1 mg to 400 mg, preferably from 200 mg to 400 mg, of the compound of Formula I or its salt. It is convenient for the subject to swallow one or two tablets, coated tablets, dragees, or gelatin capsules per day. However the composition can also be adapted for administration by any other conventional means of systemic administration including rectally, e.g. in the form of suppositories, parenterally, e.g. in the form of injection solutions, or nasally.

The active ingredients can be processed with pharmaceutically inert, inorganic or organic carriers for the production of pharmaceutical compositions. Lactose, corn starch or derivatives thereof, talc, stearic acid or its salts and the like can be used, for example, as such carriers for tablets, coated tablets, dragees and hard gelatin capsules. Suitable carriers for soft gelatin capsules are, for example, vegetable oils, waxes, fats, semi-solid and liquid polyols and the like. Depending on the nature of the active ingredient no carriers are, however, usually required in the case of soft gelatin capsules, other than the soft gelatin itself. Suitable carriers for the production of solutions and syrups are, for example, water, polyols, glycerol, vegetable oils and the like. Suitable carriers for suppositories are, for example, natural or hardened oils, waxes, fats, semi-liquid or liquid polyols and the like.

The pharmaceutical compositions can, moreover, contain preservatives, solubilizers, stabilizers, wetting agents, emulsifiers, sweeteners, colorants, flavorants, salts for varying the osmotic pressure, buffers, coating agents or antioxidants. They can also contain still other therapeutically valuable substances, particularly antidiabetic or hypolipidemic agents that act through other mechanisms. Agents which can advantageously be combined with the composition of this invention in a single formulation include but are not limited to biguanides such as metformin, insulin releasing agents such as the sulfonylurea insulin releaser glyburide and other sulfonylurea insulin releasers, cholesterol-lowering drugs such as the "statin" HMG-CoA reductase inhibitors such as atrovastatin, lovastatin, pravastatin and simvastatin, PPAR-alpha agonists such as clofibrate and gemfibrozil, alpha-glucosidase inhibitors such as acarbose (which inhibit starch digestion), and prandial insulin releasers such as repaglinide. The amounts of complementary agents combined with compositions of the invention in single formulations are in accord with the doses used in standard clinical practice. Established safe and effective dose ranges for certain representative Compounds are set forth above.

The invention will be better understood by reference to the following examples which illustrate but do not limit the invention described herein.

EXAMPLES

Example 1

Effects of Compound BI and Rosiglitazone on Body Weight of Mice with Gold Thioglucose-Induced Obesity Systemic administration of gold thioglucose (GTG) damages glucose-sensing neurons in the hypothalamus, and consequently impairs regulation of satiety, leading to chronic hyperphagia and consequent obesity. Male C57BL/6J mice, weighing 22 to 25 grams received gold thioglucose (Sigma Chemical Company, St. Louis Mo.) by intraperitoneal injection (500 mg/kg). Mice were given a high fat diet (45% Kcal fat; D12451, Research Diets, New Brunswick, N.J.) for 8 weeks to exacerbate obesity.

Mice were then divided into groups comprising 5 mice each, sorted so that each group had similar mean body weights (approximately 47 grams). Mice received single daily oral treatment with Compound BI, rosiglitazone or combinations of the two drugs. A group of lean control mice on a standard low fat rodent chow was also included.

Groups
1. Vehicle (1% hydroxypropylmethylcellulose)
2. Compound BI 30 mg/kg
3. Compound BI 100 mg/kg
4. Rosiglitazone (RSG) 3 mg/kg
5. RSG 3 mg/kg+Compound BI 30 mg/kg
6. RSG 3 mg/kg+Compound BI 100 mg/kg
7. Lean Control (no treatment)

After two weeks, blood samples were collected from the retro-orbital sinus for measurement of serum glucose, triglycerides, and free fatty acids.

Both Compound BI and rosiglitazone elicited dose-dependent decreases in blood glucose, triglycerides and free fatty acids (Table 1). Combined treatment with both agents resulted in greater decreases than did comparable doses of either agent alone.

Compound BI treatment resulted in a decrease in body weight over the course of 5 weeks (Table 2). Combined treatment with both Compound BI and rosiglitazone resulted in greater weight loss than Compound BI alone, achieveing body weights as low as lean mice on a low fat diet. Rosiglitazone alone did not reduce body weight. The combined effect of Compound BI and rosiglitazone is surprising in view of the fact that weight gain is a common side effect of rosiglitazone in humans and in some rodent models, e.g. ob/ob and db/db mice.

Treatment with Compound BI or especially Compound BI plus rosiglitazone reduced total food and calorie consumption (Table 3)

TABLE 1

Effects of Compound BI and rosiglitazone on glucose, triglycerides and free fatty acids in Gold Thioglucose-obese mice

| Group | Glucose ± SEM (mg/dL) | Triglycerides ± SEM (mg/dL) | Free Fatty Acids ± SEM (UMOL/L) |
|---|---|---|---|
| Vehicle | 266.4 ± 10.0 | 99.0 ± 6.0 | 1044.0 ± 35.9 |
| Compound BI 30 mg/kg | 205.8 ± 8.1 | 62.8 ± 3.0 | 969.2 ± 18.2 |
| Compound BI 100 mg/kg | 160.0 ± 17.7 | 53.8 ± 7.4 | 936.2 ± 63.0 |
| RSG 3 mg/kg | 215.8 ± 14.3 | 61.4 ± 4.3 | 813.8 ± 34.2 |
| RSG 3 mg/kg + Cpd. BI 30 mg/kg | 200.2 ± 8.6 | 46.0 ± 3.0* | 875.2 ± 33.0 |
| RSG 3 mg/kg + Cpd. BI 100 mg/kg | 140.8 ± 12.3 | 42.3 ± 1.3* | 804.0 ± 11.7 |
| Lean | 218.0 ± 14.8 | 137.9 ± 13.0 | 1461.8 ± 33.9 |

*p < 0.05 significantly different compared with vehicle-control

TABLE 2

Effects of Compound BI, rosiglitazone, or combinations on body weight in Gold Thioglucose-obese (GTG) mice

| | Body Weight (g ± SEM) | | | | Δ BW (g) |
|---|---|---|---|---|---|
| Group | Initial | Week 1 | Week 4 | Week 5 | 0-5 Weeks |
| Vehicle | 47.2 ± 1.2 | 50.2 ± 1.0 | 50.2. ± 0.7 | 50.2 ± 0.9 | +3.0 ± 0.4 |
| Compound BI 30 mg/kg | 47.2 ± 1.0 | 39.8 ± 0.9 | 40.0 ± 1.1* | 37.4 ± 0.9* | −9.8 ± 0.2 * |
| Compound BI 100 mg/kg | 47.5 ± 0.7 | 38.4 ± 1.1 | 34.0 ± 1.0* | 33.0 ± 1.1* | −14.6 ± 0.3 * |
| RSG 3 mg/kg | 47.4 ± 1.0 | 47.0 ± 1.0 | 46.0 ± 1.1 | 46.3 ± 1.0 | −1.2 ± 0.2 |
| RSG 3 mg/kg + Compound BI 30 mg/kg | 47.0 ± 0.7 | 38.6 ± 1.1 | 37.4 ± 0.7* | 36.4 ± 1.0* | −10.6 ± 0.3 * |
| RSG 3 mg/kg + Compound BI 100 mg/kg | 47.0 ± 0.5 | 34.6 ± 0.7 | 32.5 ± 0.6* | 27.0 ± 0.7* | −20.0 ± 0.2 * |
| Lean | 32.2 ± 0.6 | 32.4 ± 0.4 | 32.2 ± 0.6 | 30.8 ± 0.6 | −1.4 ± 0.1 |

TABLE 3

Cumulative food intake in GTG-obese mice treated with Compound BI, Rosiglitazone, or both agents for 5 weeks (grams per cage of 5 mice)

| Group | Cumulative Food Intake (grams) | Cumulative Food Intake (KCal) |
|---|---|---|
| Vehicle | 325 | 1528 |
| Compound BI 30 mg/kg | 223 | 1048 |
| Compound BI 100 mg/kg | 192 | 902 |
| RSG 3 mg/kg | 275 | 1293 |
| RSG 3 mg/kg + Compound BI 30 mg/kg | 242 | 1137 |
| RSG 3 mg/kg + Compound BI 100 mg/kg | 183 | 860 |
| Lean | 206 | 659 |

Example 2

Effects of Combinations of Compound BI and Rosiglitazone on Diabetes and Obesity in Db/Db Mice Male db/db mice have a defect in the receptor for the appetite-regulating protein leptin and consequently develop hyperphagia, obesity, insulin resistance, hyperglycemia, hypertriglyceridemia. Male db/db mice are an accepted animal model for Type II diabetes. The effect of a range of single daily doses of orally administered Compound BI was assessed in this model, and the efficacy of rosiglitazone alone and in combination with Compound BI was also examined.

Rosiglitazone is a therapeutic agent used for treatment of Type II diabetes that acts primarily via the PPAR-gamma receptor, thereby increasing the sensitivity of adipose tissue to insulin and reducing serum glucose, triglycerides, and free fatty acids. Rosiglitazone and other thiazolidinediones (TZD) often cause weight gain as a side effect, which is undesirable in a patient population that is already generally overweight, since obesity is a risk factor for Type II diabetes.

Male C57BL/Ksola db/db mice ("db/db mice") were obtained from Harlan (Indianapolis, Ind.) and allowed to acclimate for a minimum of one week. Animals received Purina 5008 Lab Diet and tap water ad libitum and were housed with 3-4 animals per cage. Male C57BL/6 mice of the same age were used as lean nondiabetic controls.

Test Agents and Vehicle:
1. Compound BI (synthesized at Wellstat Therapeutics)
2. Hydroxypropylmethylcellulose (HPMC; Sigma Chemical Co, St. Louis Mo., Cat # H7509)
3. Rosiglitazone (GlaxoSmithKline)

Body weights and blood glucose levels were measured and animals were sorted groups of 6-7 mice with equivalent mean body weights in each group. Each test group comprised five mice.

Experimental Groups:
1. Lean Control (no treatment)
2. Vehicle
3. Compound BI 30 mg/kg/day
4. Compound BI 100 mg/kg/day
5. Compound BI 150 mg/kg/day
6. Rosiglitazone 3 mg/kg
7. Rosiglitazone 3 mg/kg+Compound BI 30 mg/kg
8. Rosiglitazone 3 mg/kg+Compound BI 100 mg/kg
9. Rosiglitazone 20 mg/kg
10. Rosiglitazone 20 mg/kg+Compound BI 30 mg/kg
11. Rosiglitazone 20 mg/kg+Compound BI 100 mg/kg Drug preparation: Compound BI was suspended in a vehicle comprising 1% aqueous hydroxypropylmethylcellulose, using a tissue homogenizer to minimize particle size and maximize uniformity of the suspension. Rosiglitazone was suspended in the same vehicle. Drug concentrations in the dosing suspension for each treatment group were adjusted according to body weights so that a constant volume of 0.4 ml provided appropropriate drug doses in all groups.

Drug Administration: Drugs were administered orally by gavage once per day for 28 days.

Blood sampling: For serum chemistry analysis, nonfasting blood samples (200 microliters) were obtained via the retro-orbital sinus and collected in serum separator tubes at 11 AM on days 14 and 28 after initiation of drug administration.

Results:

All db/db mice included in the study displayed hyperglycemia prior to treatment. At all time points thereafter, Vehicle-treated mice displayed continued severe nonfasting hyperglycemia at all time points.

Compound BI treatment resulted in dose dependent reduction of serum glucose. Rosiglitazone treatment also caused a dose dependent lowering of serum glucose.

Combined treatment with Compound BI and rosiglitazone resulted in a greater reduction of serum glucose than either agent alone. Maximum glucose lowering was achieved at lower dose of both drugs in the combinations, e.g. 3 mg/kg/day rosiglitazone and 30 mg/kg Compound BI. At the higher dose of rosiglitazone (20 mg/kg), addition of Compound BI at both 30 and 100 mg/kg resulted in lower glucose levels than was achieved at maximum doses of either agent alone.

TABLE 4

Serum glucose in db/db mice treated with Compound BI, rosiglitazone or both agents for 4 weeks

| | Serum Glucose (mg/dL) | | |
|---|---|---|---|
| | Mean | SD | SEM |
| Control (Lean) | 209.8 | 3.6 | 1.6 |
| Vehicle HPMC 1% | 762.1 | 54.8 | 20.7 |
| Compound BI 30 mg/kg | 657.8 | 63.3 | 25.8 |
| Compound BI 100 mg/kg | 330.3* | 157.9 | 59.7 |
| Compound BI 150 mg/kg | 271.7* | 110.8 | 45.2 |
| RSG 3 mg/kg | 382.8 | 132.9 | 54.3 |
| RSG 20 mg/kg | 344.7 | 125.5 | 47.4 |
| RSG 3 + Cpd. BI - 30 mg/kg | 205.8* | 56 | 28 |
| RSG 3 + Cpd. BI - 100 mg/kg | 208.5* | 49.8 | 24.9 |
| RSG 20 + Cpd. BI - 30 mg/kg | 331.8 | 147.4 | 73.7 |
| RSG 20 + Cpd. BI - 100 mg/kg | 284.2* | 117.2 | 47.9 |

*Glucose less than Vehicle, P < .05

TABLE 5

Serum triglycerides in db/db mice treated with Compound BI, rosiglitazone or both agents for 4 weeks

| | Serum Triglycerides (mg/dL) | | |
|---|---|---|---|
| Groups | Mean | SD | SEM |
| Control (Lean) | 123 | 22.3 | 10 |
| Vehicle HPMC 1% | 507 | 56.3 | 21.3 |
| Compound BI 30 mg/kg | 281.2* | 98.8 | 40.3 |
| Compound BI 100 mg/kg | 179.1* | 76.7 | 29 |
| Compound BI 150 mg/kg | 177.7* | 51 | 20.8 |
| RSG 3 mg/kg | 99.2* | 17.1 | 7 |
| RSG 20 mg/kg | 117.3* | 26.3 | 9.9 |
| RSG 3 + Cpd. BI - 30 mg/kg | 71.5* | 14.5 | 7.2 |
| RSG 3 + Cpd. BI - 100 mg/kg | 85* | 21.6 | 10.8 |
| RSG 20 + Cpd. BI - 30 mg/kg | 101.5* | 9.3 | 4.6 |
| RSG 20 + Cpd. BI - 100 mg/kg | 113.3* | 26.8 | 11 |

*Lower than vehicle value, P < .05

Combined treatment with rosiglitazone at a dose of 3 mg/kg/day and Compound BI at either 30 or 100 mg/kg/day resulted in body weight loss relative to vehicle treated animals, or animals treated with either drug alone (Table 6).

TABLE 6

Body weights of db/db mice treated with Compound BI, rosiglitazone or both agents for 4 weeks

| Groups | Body Weight (grams) Mean ± SD | | Change in Body Weight (grams) |
|---|---|---|---|
| | Initial | 4 Weeks | |
| Control (Lean) | 21.8 ± 0.7 | 26.2 ± 0.8 | +4.4 |
| Vehicle db/db | 41.9 ± 1.3 | 51.2 ± 1.8 | +9.3 |
| Compound BI 30 mg/kg | 41.9 ± 0.6 | 50.3 ± 2.1 | +8.4 |
| Compound BI 100 mg/kg | 41.5 ± 0.9 | 47.8 ± 3.6 | +6.3 |
| Compound BI 150 mg/kg | 41.8 ± 0.8 | 47.4 ± 2.7 | +6.6 |
| RSG 3 mg/kg | 41.8 ± 0.9 | 48.2 ± 2.6 | +6.4 |
| RSG 20 mg/kg | 41.1 ± 1.2 | 51.4 ± 1.4 | +10.3 |
| RSG 3 + Cpd. BI - 30 mg/kg | 41.6 ± 0.9 | 31.3 ± 4.1* | −10.3* |
| RSG 3 + Cpd. BI - 100 mg/kg | 40.6 ± 0.9 | 35.0 ± 5.0* | −5.6* |
| RSG 20 + Cpd. BI - 30 mg/kg | 41.2 ± 1.7 | 42.5 ± 5.2* | +1.3* |
| RSG 20 + Cpd. BI - 100 mg/kg | 41.6 ± 2.2 | 47.0 ± 4.3 | +5.2 |

*$p < 0.05$ compared to Vehicle

Food consumption was also affected by drug treatment. Vehicle-treated mice were hyperphagic, consuming an average of more than 7 grams of chow per day, reflecting both the primary leptin receptor defect and the secondary hyperphagic effects of diabetes.

Mice treated with the combination of 3 mg/kg RSG plus 30 or 100 mg/kg Compound BI displayed a striking reduction in food consumption relative to vehicle-treated animals or those receiving either drug alone.

TABLE 7

Food consumption in db/db mice treated with Compound BI, rosiglitazone or both agents for 4 weeks

| Groups | Food Consumption (grams/24 hr/mouse) | | |
|---|---|---|---|
| | Week 2 | Week 3 | Week 4 |
| Control (Lean) | 2.6 | 2.6 | 3.4 |
| Vehicle HPMC 1% | 7.1 | 7.1 | 8 |
| Compound BI 30 mg/kg | 5.3 | 4.9 | 5.6 |
| Compound BI 100 mg/kg | 3.6 | 3.7 | 5.1 |
| Compound BI 150 mg/kg | 3.1 | 4.1 | 6 |
| RSG 3 mg/kg | 5.3 | 4.0 | 4.8 |
| RSG 20 mg/kg | 5.4 | 5.9 | 6.3 |
| RSG 3 + Cpd. BI - 30 mg/kg | 1.2 | 2.2 | 1.8 |
| RSG 3 + Cpd. BI - 100 mg/kg | 2.4 | 3.2 | 3.0 |
| RSG 20 + Cpd. BI - 30 mg/kg | 1.9 | 4.8 | 3.2 |
| RSG 20 + Cpd. BI - 100 mg/kg | 3.5 | 3.3 | 3.0 |

Compound BI treatment resulted in a dose-dependent attenuation of hyperglycemia, hypertriglyceridemia and free fatty acid levels in db/db mice. Rosiglitazone also reduced these markers of diabetes and dyslipidemia. Combined treatment with a low dose of rosiglitazone (3 mg/kg/day) and a low dose of Compound BI (30 mg/kg/day) resulted in a better therapeutic effect than did higher doses of either drug alone, or higher doses of both drugs given together. Surprisingly, the combination of low-dose RSG and Compound BI caused weight loss greater than that produced by Compound BI alone, along with a strong attenuation of hyperphagia associated with the db/db genetic defect. This is unlikely to have been a toxic anorexia, since higher doses of either RSG or Compound BI, alone or in combination, resulted in greater food intake than did the combination of the lower doses of both RSG and Compound BI.

Example 3

Effect of Compound BI in Combination with Rosiglitazone on Food Intake and Body Weight of Male C57B1/6 Mice Animals. Male C57B1/6 mice, 18 weeks of age, were housed 5/cage and fed a normal diet and tap water ad libitum for at least one month. The food intake of the animals was monitored for 3 weeks, after which they were trained to eat a single meal from 9 AM-2 PM every day. Food was withheld for the remainder of each day. Because of the restricted feeding time, the mice eat less than under ad libitum food availability. Therefore, reduction of food intake in this model requires a drug effect sufficient to overcome the hunger stimulus provided by subnormal daily food intake.

Drug Administration. Groups of 10 mice each (individually weighed and marked, divided into 5/cage and trained and monitored as above; were dosed once per day with Compound BI (100 mg/kg), rosiglitazone (3 mg/kg), both drugs, or vehicle by oral gavage at 8 AM for four consecutive days. Comparator groups receiving appetite modulators not suitable for oral dosing (PYY and cerulenin) received intraperitoneal injections at 8 AM for four consecutive days. For the first three days, all groups received their meals from 9 AM-2 PM and food intake and body weight were measured Experimental Groups

| Group # (10 animals/group) | |
|---|---|
| Oral Gavage | |
| 1 | Untreated |
| 2 | Vehicle |
| 3 | Compound BI (100 mg/kg/day) |
| 4 | Rosiglitazone (3 mg/kg) |
| 5 | Rosiglitazone + Compound BI |
| i.p. Injection | |
| 6 | Saline (3 ml/kg/day) |
| 7 | PYY (100 ug/kg in saline) |
| 8 | Cerulenin (30 mg/kg) |

Of the drugs and drug combinations tested, only the combination of Compound BI plus rosiglitazone produced a significant reduction of food intake in this restricted feeding paradigm. The known appetite modulators PYY and Cerulenin failed to have an effect in this model system.

TABLE 8

Food intake before and after drug treatment

| Groups | Pretreatment Food Intake (Unrestricted) (grams ± SEM) | Pretreatment Food Intake (5 Hour) | Post-treatment Food Intake (5 Hour) |
|---|---|---|---|
| Untreated | 4.11 ± 0.10 | 3.20 ± 0.09 | 2.24 ± 0.19 |
| Vehicle PO | 3.86 ± 0.14 | 3.00 ± 0.08 | 2.06 ± 0.16 |
| Compound BI (100 mg/kg) | 3.58 ± 0.11 | 2.99 ± 0.07 | 2.00 ± 0.18 |
| Rosiglitazone (3 mg/kg) | 3.55 ± 0.16 | 2.94 ± 0.07 | 2.21 ± 0.15 |
| Rosiglitazone (3 mg/kg + Compound BI (100 mg/kg) | 3.93 ± 0.20 | 3.08 ± 0.08 | 1.74 ± 0.13* |

TABLE 8-continued

Food intake before and after drug treatment

| Groups | Pretreatment Food Intake (Unrestricted) (grams ± SEM) | Pretreatment Food Intake (5 Hour) | Post-treatment Food Intake (5 Hour) |
|---|---|---|---|
| Saline IP | 3.91 ± 0.09 | 3.04 ± 0.10 | 2.46 ± 0.24 |
| PYY (100 mg/kg) | 4.07 ± 0.11 | 3.02 ± 0.07 | 2.28 ± 0.25 |
| Cerulenin (30 mg/kg) | 3.90 ± 0.21 | 2.93 ± 0.08 | 2.45 ± 0.10 |

*p < 0.05 significantly different compared with vehicle-control

In accord with the effects on food intake, only the combination of Compound BI plus rosiglitazone resulted in a significant reduction of body weight in this short-term experimental design.

TABLE 9

Body weights before and after drug treatments

| Groups | Pretreatment Body weight (grams ± SEM) | Post-treatment Body weight | Change in Body weight (grams ± SEM) |
|---|---|---|---|
| Untreated | 21.30 ± 0.33 | 20.85 ± 0.31 | −0.45 ± 0.11 |
| Vehicle PO | 21.25 ± 0.49 | 20.85 ± 0.45 | −0.40 ± 0.12 |
| Compound BI (100 mg/kg) | 20.97 ± 0.50 | 20.57 ± 0.51 | −0.40 ± 0.15 |
| Rosiglitazone (3 mg/kg) | 20.88 ± 0.42 | 20.76 ± 0.39 | −0.12 ± 0.09 |
| Rosiglitazone (3 mg/kg + Compound BI (100 mg/kg) | 20.91 ± 0.77 | 18.18 ± 0.78 | −2.73 ± 0.16* |
| Saline IP | 21.01 ± 0.59 | 20.99 ± 0.63 | −0.02 ± 0.16 |
| PYY (100 mg/kg) | 21.06 ± 0.29 | 20.86 ± 0.33 | −0.20 ± 0.10 |
| Cerulenin (30 mg/kg) | 21.02 ± 0.68 | 21.18 ± 0.66 | +0.16 ± 0.10 |

TABLE 10

Percent body weight changes

| Groups | Change in Body weight % |
|---|---|
| Untreated | −2.11 ± 0.52 |
| Vehicle PO | −1.84 ± 0.54 |
| Compound BI (100 mg/kg) | −1.90 ± 0.73 |
| Rosiglitazone (3 mg/kg) | −0.55 ± 0.44 |
| Rosiglitazone (3 mg/kg + Compound BI (100 mg/kg) | −14.02 ± 0.80 |
| Saline IP | −0.12 ± 0.78 |
| PYY (100 mg/kg) | −0.96 ± 0.50 |
| Cerulenin (30 mg/kg) | +0.81 ± 0.49 |

Example 4

Effects of Compound BI, Compound CF, and Compound CT Alone and in Combination with Rosiglitazone on Serum Glucose and Adiponectin in Db/Db Mice Adiponectin is an glycoprotein secreted from white adipose tissue. Adiponectin improves insulin sensitive in other tissues, e.g. muscle and liver, and is also protective against atherosclerosis. Thiazolidinedione antidiabetic agents such as rosiglitazone or pioglitazone act largely via action at the PPAR-gamma, a nuclear receptor involved in regulation of fuel metabolism. PPAR-gamma agonists enhance adiponectin production by adipose tissue, and this may contribute to their beneficial effects in diabetes and related metabolic disorders.

Groups
  8. Vehicle (1% hydroxypropylmethylcellulose)
  9. Compound BI 100 mg/kg
  10. Rosiglitazone (RSG) 3 mg/kg
  11. Compound BI 100 mg/kg+RSG 3 mg/kg
  12. Compound CF 100 mg/kg
  13. Compound CF 100 mg/kg+RSG 3 mg/kg
  14. Compound CT 100 mg/kg+RSG 3 mg/kg
  15. Compound CT 100 mg/kg+RSG 3 mg/kg After two weeks, blood samples were collected from the retro-orbital sinus and processed for serum chemistry measurements.

Rosiglitazone by itself slightly elevated serum adiponectin. Compound BI, Compound CF and Compound CT as individual agents did not elevate serum adiponectin levels, but they did strongly amplify the effect of concurrent rosiglitazone on adiponectin.

TABLE 11

Effects of Compound BI, Compound CF, and Compound CT alone and in combination with rosiglitazone on serum glucose and adiponectin in db/db mice

| Group | Glucose ± SD (mg/dL) | Adiponectin ± SD (micrograms/ml) |
|---|---|---|
| Vehicle | 305 ± 39 | 8.0 ± 1.7 |
| Compound BI 100 mg/kg | 206 ± 44 | 9.3 ± 4.8 |
| RSG 3 mg/kg | 258 ± 74 | 12.3 ± 3.0* |
| Compound BI 100 mg/kg + RSG 3 mg/kg | 159 ± 93 | 21.0 ± 8.4* |
| Compound CF 100 mg/kg | 305 ± 75 | 6.5 ± 2.0 |
| Compound CF 100 mg/kg + RSG 3 mg/kg | 190 ± 119 | 19.1 ± 4.5* |
| Compound CT 100 mg/kg | 235 ± 107 | 5.4 ± 1.5 |
| Compound CT 100 mg/kg + RSG 3 mg/kg | 251 ± 113 | 19.1 ± 5.2* |

*p < 0.05 significantly different compared with vehicle-control

Example 5

Effects of Combinations of Compound BI and Rosiglitazone or Pioglitazone on Serum Glucose in Db/Db Mice Male db/db mice have a defect in the receptor for the appetite-regulating protein leptin and consequently develop hyperphagia, obesity, insulin resistance, hyperglycemia, hypertriglyceridemia. Male db/db mice are an accepted animal model for Type II diabetes. The effect of a range of single daily doses of orally administered Compound BI was assessed in this model, and the efficacy of rosiglitazone alone and in combination with Compound BI was also examined.

Rosiglitazone and pioglitazone are therapeutic agents used for treatment of Type II diabetes and which act primarily via the PPAR-gamma receptor, thereby increasing the sensitivity of adipose tissue to insulin and reducing serum glucose, triglycerides, and free fatty acids. Rosiglitazone, pioglitazone and other thiazolidinediones (TZD) often cause weight gain as a side effect, which is undesirable in a patient population that is already generally overweight.

Male C57BL/Ksola db/db mice ("db/db mice") were obtained from Harlan (Indianapolis, Ind.) and allowed to acclimate for a minimum of one week. Animals received Purina 5008 Lab Diet and tap water ad libitum and were housed with 3-4 animals per cage.

Test Agents and Vehicle:
 4. Compound BI (synthesized at Welistat Therapeutics Corp.)
 5. Hydroxypropylmethylcellulose (HPMC; Sigma Chemical Co, St. Louis Mo., Cat #H7509)
 6. Rosiglitazone (GlaxoSmithKline)
 7. Pioglitazone (Lilly)

Body weights and blood glucose levels were measured and animals were sorted groups of 6-7 mice with equivalent mean body weights in each group. Each test group comprised five mice.

Experimental Groups:
 12. Vehicle
 13. Compound BI 100 mg/kg/day
 14. Rosiglitazone 3 mg/kg
 15. Rosiglitazone 3 mg/kg+Compound BI 100 mg/kg
 16. Pioglitazone 30 mg/kg
 17. Pioglitazone 30 mg/kg+Compound BI 100 mg/kg
 18. Pioglitazone 100 mg/kg
 19. Pioglitazone 100 mg/kg+Compound BI 100 mg/kg Drug preparation: Compound BI was suspended in a vehicle comprising 1% aqueous hydroxypropylmethylcellulose, using a tissue homogenizer to minimize particle size and maximize uniformity of the suspension. Pioglitazone and rosiglitazone were suspended in the same vehicle after pulverization of commercial tablets of each of these drugs. Drug concentrations in the dosing suspension for each treatment group were adjusted according to body weights so that a constant volume of 0.4 ml provided appropropriate drug doses in all groups.

Drug Administration: Drugs were administered orally by gavage once per day for 28 days.

Blood sampling: For serum chemistry analysis, nonfasting blood samples (200 microliters) were obtained via the retro-orbital sinus and collected in serum separator tubes at 11 AM on day 28 after initiation of drug administration.

Results:

All db/db mice included in the study displayed hyperglycemia prior to treatment. At all time points thereafter, Vehicle-treated mice displayed continued severe nonfasting hyperglycemia at all time points.

Combined treatment with Compound BI and rosiglitazone resulted in a greater reduction of serum glucose than either agent alone. Pioglitazone alone had a relatively small effect on serum glucose, but combinations with Compound BI lowered glucose better than either agent alone.

TABLE 12

Serum glucose in db/db mice treated with Compound BI, rosiglitazone, pioglitazone or combinations for 4 weeks

| Treatment Group | Serum Glucose (mg/dL) Mean ± SD |
|---|---|
| Vehicle HPMC 1% | 622 ± 155 |
| Compound BI 100 mg/kg | 376 ± 151 |
| Rosiglitazone (RSG) 3 mg/kg | 432 ± 138 |
| RSG 3 mg/kg + Compound BI 100 mg/kg | 215 ± 31 |
| Pioglitazone (PIO) 30 mg/kg | 550 ± 74 |
| PIO 100 mg/kg | 597 ± 228 |
| PIO 30 mg/kg + Compound BI 100 mg/kg | 284 ± 46 |
| PIO 100 mg/kg + Compound BI 100 mg/kg | 247 ± 73 |

*Glucose less than Vehicle, P < .05

Example 6

Effects of Compound BI and Rosiglitazone on Expression of Uncoupling Protein 1 in White Adipose Tissue in Db/Db Mice Mice bearing the db/db mutation have a defect in leptin signaling, leading to hyperphagia, obesity and diabetes.

Uncoupling Protein 1 (UCP1) is a protein that can dissipate metabolic energy when expressed in the mitochondrial membrane. It is present in brown adipose tissue (BAT; the brown color is due to a higher density of mitochondria than in white adipose tissue) in small mammals where its main function is to generate heat, but it can also serve to accelerate combustion of fatty acids. This latter function is especially important when UCP1 is expressed in tissues other than brown fat, since depots of brown fat are limited in humans Expression of UCP1 in white fat alters the functional phenotype of the tissue from fat storage to fat combustion. Transgenic mice expressing UCP1 in white adipose tissue are resistant to obesity and diabetes induced by a high fat diet. Pharmacological induction of UCP1 expression in white adipose tissue is therefore an attractive strategy for promoting weight reduction and resistance to body weight gain.

Male obese (db/db homozygote) C57BL/Ksola mice approximately 8 weeks of age, were obtained from Jackson Labs (Bar Harbor, Me.) and randomly assigned into groups of 5-7 animals such that the body weights (40-45 g) and serum glucose levels ($\geqq 300$ mg/dl in fed state) were similar between groups; male lean (db/+ heterozygote) mice served as cohort controls. A minimum of 7 days was allowed for adaptation after arrival. All animals were maintained under controlled temperature (23° C.), relative humidity (50±5%) and light (7:00-19:00), and allowed free access to standard chow (Formulab Diet 5008, Quality Lab Products, Elkridge, Md.) and water.

Treatment cohorts were given daily oral doses of vehicle, Compound BI (100 mg/kg/day), rosiglitazone (RSG; 3 mg/kg/day) or a combination of the two drugs for 2 weeks. At the end of the treatment period epididymal fat pads were excised, frozen and subsequently processed for measurement of UCP1 by Western Blot analysis. Blood samples were also collected prior to sacrifice via the retro-orbital plexus, and processed and analyzed for serum glucose (AniLytics, Inc.; Gaithersburg Md.).

White adipose tissue lysates were resolved by electrophoresis on a 17×15×0.15 cm gel in 8.5% PAG, TRIS-Gly-SDS. The gel was electrotransfered onto an IMMOBILON membrane and blocked in 3% non-fat milk in TBST (25 mM Tris-HCL; 0.1% Tween 20) overnight in a cold room.

The membrane was washed 3 times in TBST at room temperature, and then incubated with a primary anti UCPI antibody (Chemicon Rabbit anti-mouse UCP-1, catalogue #AB3036) for 1 hr at RT (room temperature) in a sealed bag. After 1 hr with primary antibody, the membrane was washed 6×7 min in TBST at room temperature, and incubated with secondary antibody for 1 hr (Anti-Rabbit-HRP (Amersham). Working dilution: 20 µL in 100 mL TBST). The membrane was washed 6×7 min in TBST at room temperature, and then incubated with ECL (enhanced chemiluminescence) reagent (Amersham) for 1 min, and the relative amounts of UCP1 in tissue samples were quantified by densitometry of the images on X-ray film resulting from exposure to light from the chemiluminescence reaction, and expressed as relative light units (RLU).

Compound BI alone slightly the UCP1 content of elevated white adipose tissue. Rosiglitazone by itself had a larger effect, and a combination of Compound BI and rosiglitazone very strongly increased expression of UCP1, as shown in Table 13. Compound BI and rosiglitazone individually reduced serum glucose relative to vehicle treated control animals, and the combination of Compound BI and rosiglitazone reduced glucose to a greater degree than did either drug alone (Table 13).

TABLE 13

Effects of Compound BI and Rosiglitazone on serum glucose and UCP1 content of white adipose tissue (WAT) in db/db mice treated for two weeks

| Groups | Glucose mg/dL | Glucose (% Control) | WAT UCP1 (relative light units) |
|---|---|---|---|
| Lean-Control | 263.2 ± 59.0* | 38 ± 8* | 89 ± 24 |
| Vehicle (Control) | 688.5 ± 35.0 | 100 ± 5 | 124 ± 7 |
| Cpd. BI - 100 mg/kg | 302.0 ± 40.7* | 44 ± 6* | 322 ± 94* |
| RSG-3 mg/kg | 403.7 ± 28.0 | 59 ± 4 | 2067 ± 717* |
| RSG 3 + Cpd. BI 100 | 216.5 ± 18.4* | 31 ± 3* | 20683 ± 11546* |

*$p < 0.05$ significantly different compared with vehicle-control

What is claimed is:

1. A method of treating a mammalian subject having a condition selected from the group consisting of insulin resistance syndrome and Type II Diabetes, comprising administering to the subject a Compound of Formula I or a pharmaceutically acceptable salt thereof

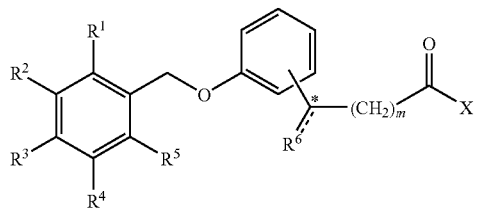

wherein:
m is 0, 2 or 4; and
X is —$OR^7$, wherein $R^7$ is hydrogen or alkyl having from 1 to 3 carbon atoms;
$R^6$ is hydrogen, O or hydroxy; and
three of $R^1$, $R^2$, $R^3$, $R^4$ and $R^5$ are hydrogen and the remainder are independently selected from the group consisting of hydrogen, halo, hydroxy, methyl, ethyl, perfluoromethyl, methoxy, ethoxy, and perfluoromethoxy;
or X is —$NR^8R^9$, wherein $R^8$ is hydrogen or hydroxy and $R^9$ is hydrogen, methyl or ethyl;
$R^6$ is hydrogen; and
three of $R^1$, $R^2$, $R^3$, $R^4$ and $R^5$ are hydrogen and the remainder are independently selected from the group consisting of hydrogen, halo, methyl, ethyl, perfluoromethyl, methoxy, ethoxy, and perfluoromethoxy;
and a direct PPAR-gamma agonist in a combined amount effective to treat the metabolic condition
wherein the Compound of Formula I or salt thereof is administered in an amount that is less than the usual therapeutic dose when administered alone.

2. The method of claim 1, wherein the Compound is represented by Formula IA

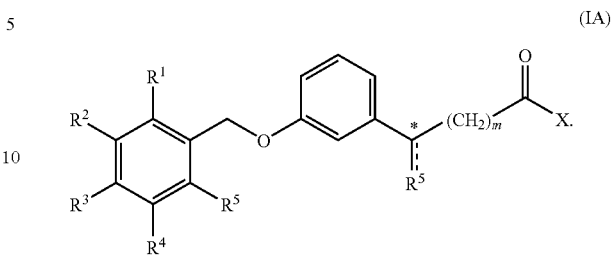

3. The method of claim 2, wherein $R^1$ is methyl and $R^5$ is methyl.
4. The method of claim 3, wherein the Compound is 4-(3-(2,6-Dimethylbenzyloxy)phenyl)-4-oxobutyric acid.
5. The method of claim 3, wherein the Compound is 3-(2,6-Dimethylbenzyloxy)-phenylacetic acid.
6. The method of claim 3, wherein the Compound is 4-3-(2,6-Dimethylbenzyloxy)-phenyl)-4(R)-hydroxybutanoic acid.
7. The method of claim 3, wherein the Compound is N-Hydroxy-2-[3-(2,6-dimethylbenzyloxy)phenyl]acetamide.
8. The method of claim 1, wherein the direct PPAR-gamma agonist is selected from the group consisting of rosiglitazone and pioglitazone, their pharmaceutically acceptable salts, hydrates, and solvates, and hydrates and solvates of such salts.
9. The method of claim 1, wherein the direct PPAR-gamma agonist is selected from the group consisting of:
5-[(2,4-dioxothiazolidin-5-yl)methyl]-2-methoxy-N-[[4-(trifluoromethyl)-phenyl]methyl]benzamide;
(+)-5-[[6-(2-fluorbenzyl)-oxy-2-naphy]methyl]-2,4-thiazolidinedione;
4-[4-[2-(5-methyl-2-phenyl-4-oxazolyl)ethoxy]benzyl]-3,5-isoxazolidinedione);
(−)$_3$-[4-[2-(Phenoxazin-10-yl)ethoxy]phenyl]-2-ethoxypropanoic acid;
[5-[4-[2-(1-indolyl)ethoxy]phenyl]methyl]thiazolidine-2,4-dione;
5-[4-[2-(5 methyl-2-phenyl-4-oxazolyl)-2-hydroxyethoxy]benzyl]-2,4-thiazolidinedione;
(S)-2-ethoxy-3-[4-[2-(4-methylsulphonyloxyphenyl)ethoxy]phenyl]propanoic acid;
and {[±]-5-[(7-benzyloxy-3-quinolyl)methyl]-2,4-thiazolidinedione}.
10. The method of claim 1, wherein the subject is a human.
11. The method of claim 1, wherein the direct PPAR-gamma agonist is administered in an amount that is less than the usual therapeutic dose when administered alone.
12. The method of claim 1, wherein the combined amount is selected so that the treatment results in one or more of weight loss and appetite reduction in the subject.
13. The method of claim 1, wherein the direct PPAR-gamma agonist and the Compound of Formula I are mixed together to form an admixture and the admixture is administered to the subject.
14. The method of claim 1, wherein the direct PPAR-gamma agonist and the Compound of Formula I are not mixed together to form an admixture but are administered independently to the subject.

* * * * *